(12) United States Patent
Liu et al.

(10) Patent No.: US 9,829,464 B2
(45) Date of Patent: Nov. 28, 2017

(54) LIQUID SAMPLING DEVICE FOR USE WITH MOBILE DEVICE AND METHODS

(71) Applicant: The Board of Trustees of the University of Illinois, Urbana, IL (US)

(72) Inventors: Gang Logan Liu, Champaign, IL (US); Manas Ranjan Gartia, Urbana, IL (US); Te-Wei Chang, Urbana, IL (US); Xinhao Wang, Urbana, IL (US); Jing Jang, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 477 days.

(21) Appl. No.: 14/383,522

(22) PCT Filed: Mar. 13, 2013

(86) PCT No.: PCT/US2013/030959
§ 371 (c)(1),
(2) Date: Sep. 5, 2014

(87) PCT Pub. No.: WO2013/138487
PCT Pub. Date: Sep. 19, 2013

(65) Prior Publication Data
US 2015/0127271 A1    May 7, 2015

Related U.S. Application Data

(60) Provisional application No. 61/611,076, filed on Mar. 15, 2012.

(51) Int. Cl.
*G06F 19/00* (2011.01)
*G01N 27/416* (2006.01)
(Continued)

(52) U.S. Cl.
CPC ......... *G01N 27/4166* (2013.01); *G01N 33/18* (2013.01); *G01N 33/182* (2013.01);
(Continued)

(58) Field of Classification Search
CPC .......... G01N 2035/00326; G01N 2035/00495; G01N 35/0092
(Continued)

(56) References Cited

U.S. PATENT DOCUMENTS

2001/0053970 A1    12/2001    Ford et al.
2007/0116600 A1    5/2007    Kochar et al.
(Continued)

FOREIGN PATENT DOCUMENTS

CN    1322949    11/2001
CN    2694271    4/2005
(Continued)

OTHER PUBLICATIONS

Chen, X. et al., Walking Along Le Water: Environmental Protection Class by River, *Livelihood Weekly*, No. 26 (Dec. 2011).
(Continued)

*Primary Examiner* — Edward Raymond
(74) *Attorney, Agent, or Firm* — Klarquist Sparkman, LLP

(57) ABSTRACT

A liquid sampling device for use with a mobile device comprises a wired connection for connecting the liquid sampling device to the mobile device, a sample receiving and testing section capable of receiving a liquid sample and conducting electrochemical testing of the liquid sample and a sample testing circuit configured to communicate at least one liquid sample test result to the mobile device via the wired connection. Associated methods and a mobile device application for interfacing with the liquid sampling device are also disclosed.

20 Claims, 24 Drawing Sheets

(51) Int. Cl.
*G01N 33/18* (2006.01)
*G01N 35/00* (2006.01)
*H04M 1/21* (2006.01)
*H04M 1/725* (2006.01)

(52) U.S. Cl.
CPC ........ *G01N 35/00871* (2013.01); *H04M 1/21* (2013.01); *H04M 1/72527* (2013.01)

(58) Field of Classification Search
USPC .......................................... 702/88, 182–185
See application file for complete search history.

(56) References Cited

U.S. PATENT DOCUMENTS

| | | |
|---|---|---|
| 2007/0263046 A1 | 11/2007 | Iwasa et al. |
| 2007/0281288 A1 | 12/2007 | Belkin et al. |
| 2008/0262321 A1 | 10/2008 | Erad et al. |
| 2010/0121210 A1 | 5/2010 | Lindner et al. |
| 2010/0299615 A1 | 11/2010 | Miluzzo et al. |
| 2011/0155587 A1 | 6/2011 | Shacham-Diamand et al. |
| 2013/0041236 A1* | 2/2013 | Pugia ................ A61B 10/0045 600/309 |

FOREIGN PATENT DOCUMENTS

| | | |
|---|---|---|
| CN | 101828155 | 9/2010 |
| CN | 202256243 | 5/2012 |
| CN | 102980932 | 3/2013 |
| WO | WO2011/141908 | 11/2011 |

OTHER PUBLICATIONS

Guo, C. et al., "Recent Progress of the Electrochemical Determination of Trace Amounts of Nitrites in Food," *Meat Research*, No. 10, pp. 25-28 (Dec. 2006).

Office Action from Chinese Patent Office for Chinese Patent Application No. 201380019724.4, dated Jul. 23, 2015.

Sun, D. et al., "Research on Determination Methods of Nitrate in Environmental Water," *Leather Science and Engineering*, vol. 19, No. 5, pp. 36-38 (Oct. 2009).

Zhang, Y. et al., "Self-Assembled Gold Nanoparticles Modified Electrode for Electrochemical Detection Nitrite," *Environmental Science*, vol. 32, No. 4, pp. 1127-1132 (Apr. 2011).

International Search Report for PCT/US2013/030959, dated Jun. 6, 2013, 2 pages.

Written Opinion for PCT/US2013/030959, dated Jun. 6, 2013, 6 pages.

* cited by examiner

LIQUID SAMPLING DEVICE FOR USE WITH MOBILE DEVICE AND METHODS

CROSS REFERENCE TO RELATED APPLICATIONS

This is the U.S. National Stage of International Application No. PCT/US2013/030959, filed Mar. 13, 2013, which was published in English under PCT Article 21(2), which in turn claims the benefit of U.S. Provisional Application No. 61/611,076, filed Mar. 15, 2012, which applications are herein incorporated by reference in their entirety.

BACKGROUND

Nitrogen exists in different forms in the environment and living organisms (such as in amino acids, proteins and nucleic acids (DNA), as just a few examples). The increasing use of nitrogen-containing fertilizers today can lead to eutrophication in ground water, inland fresh water sources (including lakes) and even coastal sea water. This in turn can cause algae blooms, since nitrogen is one of the main nutrients for most plants and algae. Eutrophication will result in an over-consumption of oxygen in aquatic environments and disruption of the ecological balance.

Increasing nitrate concentration in water also causes harmful effects to human health. Methaemoglobinaemia (also known as "blue baby syndrome"), which causes patients to have a significantly compromised ability to carry vital oxygen in their blood, is mainly due to excess nitrate in drinking water. In the U.S., the Environmental Protection Association (EPA) regulates the maximum allowable contamination level for nitrate as nitrogen ($NO_3$—N) to be 10 ppm (10 mg/L) so as to prevent adverse health effects on people. Nitrite ($NO_2^-$), a kind of reduced form of nitrate, is another major cause of mass fish kills in contaminated lakes and near seashores, and it is detrimental to human health as well. Therefore, effective and accurate detection of nitrate concentrations in water samples in the field has become significant and imperative.

Currently, the general public is not equipped to detect invisible contaminants such as nitrate in a water source because in general such detection requires specialized instrument and reagents, a certain level of expertise and, in some cases, high costs. In some special circumstances, it is strongly desired for people like environmental scientists, tourists and soldiers to have the ability to precisely determine nitrate contamination in environmental water sources they encounter. Therefore, an easy to operate, accurate, sensitive and portable platform for nitrate detection in the field is desirable.

Many existing methods to determine nitrate concentration are available, including spectroscopic methods, chromatography, capillary electrophoresis and electrochemistry methods. Spectroscopic methods are broadly used for nitrate determination, mainly using UV/Vis or fluorometric emission. These methods normally involve the use of chemical reactions like the Griess reaction to form highly fluorescent compounds to be compared and measured using a spectrophotometer. The detection limit achievable by these methods is in between 0.02 and 2 µM. But multiple required reaction steps make these methods time consuming. Also, the instrument for fluorescence spectroscopic detection is not readily accessible to non-scientists. Chromatography methods, either gas chromatography or ion chromatography, are commonly used in laboratory set-ups. Although the processes are relatively simple and fast in the laboratory, some requirements like high pressure for HPLC (high-pressure liquid chromatography) and a long column (200 mm) make it difficult to miniaturize these techniques. The flow rate control of the mobile phase is also sensitive to vibration or trembling and hence is unsuitable for a portable device. Further, due to the associated high costs and large form factor, it is unlikely to be adopted by everyday user for routine nitrate measurements. For capillary electrophoresis methods, the required column length is even longer and the set up for fluorescence detection is also complicated.

Compared with other methods, electrochemistry methods are relatively easy to operate and more readily transformable to a portable platform. In these electrochemical methods, application of potential between reference and working electrodes, causes oxidation or reduction of electro-active species to occur. Cyclic voltammetry is a popular method often used in electrochemistry systems. It would be helpful to apply electrochemistry methods in a portable platform approach to allow everyday users to quickly, cheaply and accurately record nitrate concentration and other similar environmental data in the field.

SUMMARY

Such a miniaturized nitrate sensor operated by a mobile device (such as a mobile phone) would be quite helpful in achieving data recording and data transmission functions, as well as associating data with time, location and user observations. Owing to the ubiquitous cell phone wireless network, measured water contamination data can be sent to internet social media platforms and collected by cloud servers for immediate and wide dissemination.

Described below are embodiments of a liquid sampling device for use with a mobile device. The liquid sampling device comprises a wired connection for connecting the liquid sampling device to the mobile device, a sample receiving and testing section capable of receiving a liquid sample and conducting electrochemical testing of the liquid sample and a sample testing circuit configured to communicate at least one liquid sample test result to the mobile device via the wired connection.

The sample receiving and testing section can comprise a sensor configured to test for nitrate concentration in the liquid sample. The sensor can comprise a reference electrode, a working electrode and a counter electrode.

The wired connection to the mobile device can comprise a wired connection to an audio jack of the mobile device or to a USB connection on the mobile device.

The sample testing circuit can comprise a modulation/demodulation circuit configured to modulate the at least one test result into an audio signal and communicate the audio signal to the mobile device via an audio jack of the mobile device.

According to another implementation, a data storage device is encoded with a computer program, comprising instructions that when executed by one or more computers cause the one or more computers to perform operations comprising receiving data from an attached liquid sampling device via a wired connection, the data comprising at least one liquid sample test result, and communicating the data and position information corresponding to the data over a network.

The method can comprise controlling a sensor in the liquid sampling device by commands entered on the mobile device and communicated via the wired connection.

The method can further comprise displaying the at least one test result on a map to indicate a location correlated with the test result.

The data storage device can be a mobile device. The one or more computers can comprise the mobile device. Receiving data can comprise receiving data via a wired connection to an audio jack of the mobile device.

The at least one liquid sample test result can comprise an indication of a nitrate concentration.

Communicating the data and position information can comprise posting the data and position information to a social network. The method can comprise displaying a signal wave settings screen and requesting a user to select at least one of a signal wave category, an amplitude range, a frequency range and a sampling rate. The method can comprise displaying a bias voltage settings screen and requesting a user to select at least one of a bias voltage, an amplitude, a frequency, a sampling rate, and a number of samples. The method can comprise displaying an analysis screen and requesting a user to input a down sampling rate.

The method can comprise displaying a parameters screen and requesting a user to specify a number of stabilizing cycles. The method can comprise displaying a parameters screen and requesting a user to specify an analysis duration.

Receiving the data can comprise receiving user data entered by a user of the liquid sampling device and wherein communicating the data and position information further comprises communicating the user data. The user data can comprise field observations entered by a user.

These and other features will become more apparent from the following detailed description of several embodiments, which proceeds with reference to the accompanying figures.

BRIEF DESCRIPTION OF THE DRAWINGS

FIG. 1b is an exploded perspective view of the liquid sampling device of FIG. 1a.

DETAILED DESCRIPTION OF PREFERRED EMBODIMENTS

Embodiments of a liquid sampling device suited for use with a mobile device (such as a mobile phone or other type of handheld mobile device), associated methods and a mobile device application for interfacing with the liquid sampling device are described below. The liquid sampling device is described for rapid electrochemical testing for nitrate concentration, such as in small samples of water, but electrochemical testing for phosphates or organic contaminants (e.g., bacteria) can be implemented as well. The mobile device can be used, e.g., to control the sampling device, to process, display, store and communicate data, and/or to allow users to post data and other comments to networks, such as a private cloud storage network and/or a public social media network. Desirably, substantially real-time test results are available to the user.

Figure 1A:
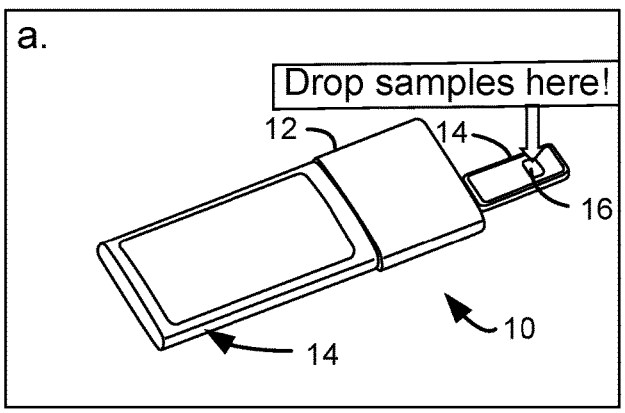
FIG. 1a is a perspective view of an exemplary liquid sampling device assembled for use with a mobile device.
Figure 1B:
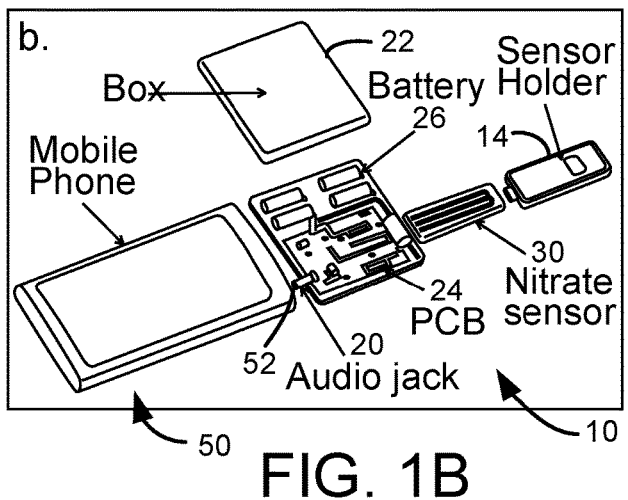
Figure 1C:
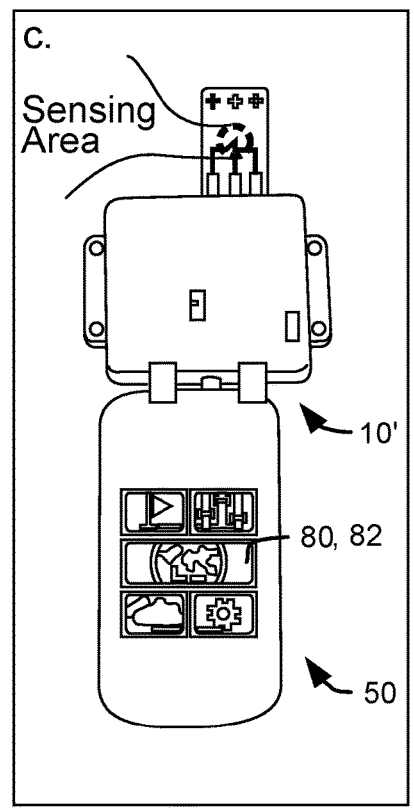
FIG. 1c is a top plan view of another exemplary liquid sampling device shown assembled with a mobile device.

A schematic depiction of implementations of the liquid sampling device is shown in FIGS. 1a-1c. FIG. 1a is a perspective view of a liquid sampling device 10 shown connected to a mobile device 50. The liquid sampling device 10 has a body 12 and a sensor holder 14 extending from the body. The sensor holder 14 has an opening 16 within which liquid to be sampled can be placed. As shown, the liquid sampling device 10 and mobile device 50 remain compact and portable even when they are coupled together as shown in FIG. 1a.

FIG. 1b is another perspective view similar to FIG. 1a, except showing the liquid sampling device 10 in an exploded format to illustrate more detail. As indicated, the liquid sampling device 10 has a wired or physical connection 20 to the mobile device 50 via an audio jack 52 of the mobile device 50. In other implementations, a connection to a USB port or another type of connector on the mobile device can be used.

A cover 22 can be removed to show a sample testing circuit 24 and a power source 26 for the sensing device, such as one or more batteries. The testing circuit 24 can be implemented in a printed circuit board as illustrated or in another suitable topology. Further details of the testing circuit 24 are described below.

The sensor holder 14 can be removable as shown to expose a sensor 30, such as one having a microfluidic sample chamber. The sensor 30 is connected to the testing circuit 24 and is described below in greater detail. The sensor 30 is sometimes referred to herein as a sample receiving and testing section.

FIG. 1c is a plan view of another liquid sampling device 10' having similar functional features but illustrating a slightly different body 12' and overall external experience. In FIG. 1C, the mobile device 50 (which in this example is a Samsung mobile phone) is illustrated running a mobile phone software application 80 for interfacing with the sampling device 10' and displaying a start screen 82.

Figure 2:
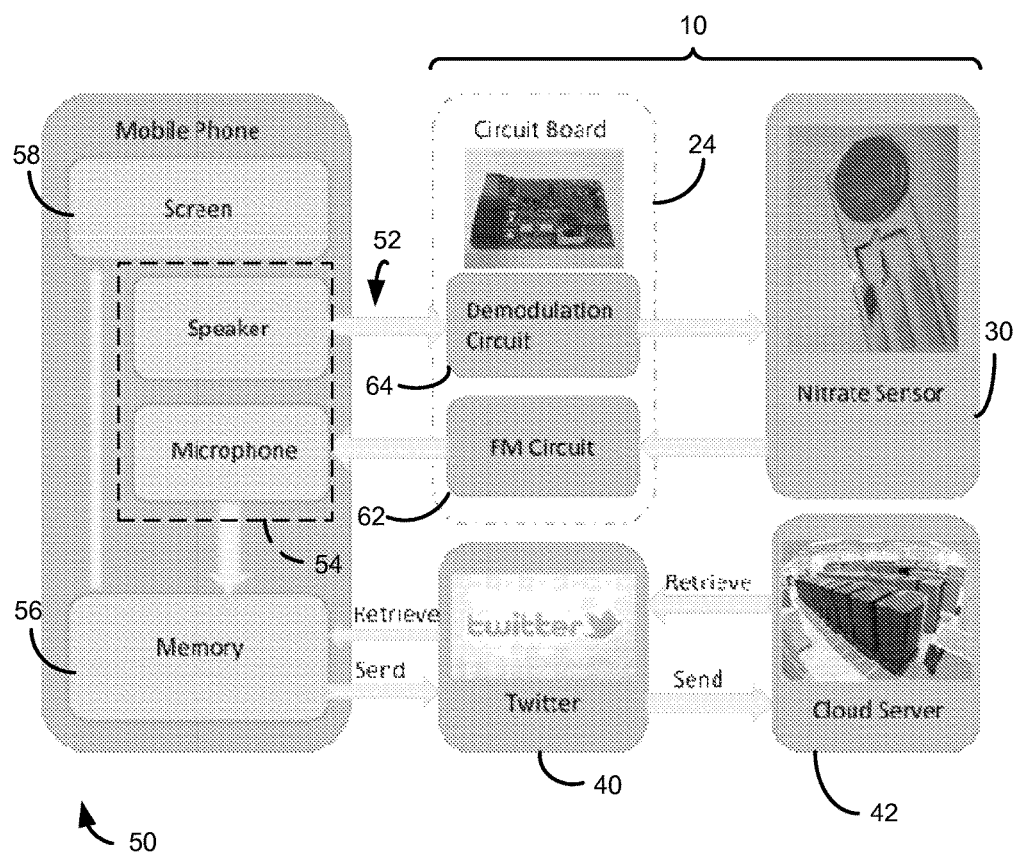
FIG. 2 is a block diagram of the liquid sampling device, the mobile device and connections to a network and servers.

FIG. 2 is a schematic block diagram illustrating structural and logical connections among the liquid sampling device 10, the mobile device 50, the sensor 30, a network 40 and cloud storage 42. Specifically, the testing circuit 24 is shown connected to the sensor 30 for controlling the sensor to initiate a sensing cycle and to receive data from the sensor, e.g., sensed readings from tests of liquid samples. In the illustrated implementation, the testing circuit 24 has frequency modulation and demodulation circuit components 62 and 64, respectively, that are connected to the sensor 30 and to the mobile device 50.

As indicated, one implementation of the wired connection of the mobile device is via the audio jack 52. Among other advantages, the common audio jack 52 is widely used by most manufacturers and thus presents a convenient interface. The frequency modulation circuit component 62 and demodulation circuit component 64 are shown connected to an audio circuit 54 (including speaker and microphone circuit components) of the mobile device 50. As also shown, a memory 56 of the mobile device is used to store data. A display 58 of the mobile device is used to display test result and other information, and to function as an interface for controlling operation of the liquid sampling device 10.

With the computing and communications capabilities of the mobile device 50, test data, observations from the field (e.g., location, weather, etc.) and other information/metadata can be posted to a private or public network 40 (even using Twitter or other social media tools), or to cloud storage 42 or another type of data storage. Information can be downloaded from such networks and storage facilities, too. For example, in the case of a user interested in seeing data for her surrounding area, she can download a relevant map showing nitrate concentration data for samples tested near the current location detected from her mobile device.

Figure 4:
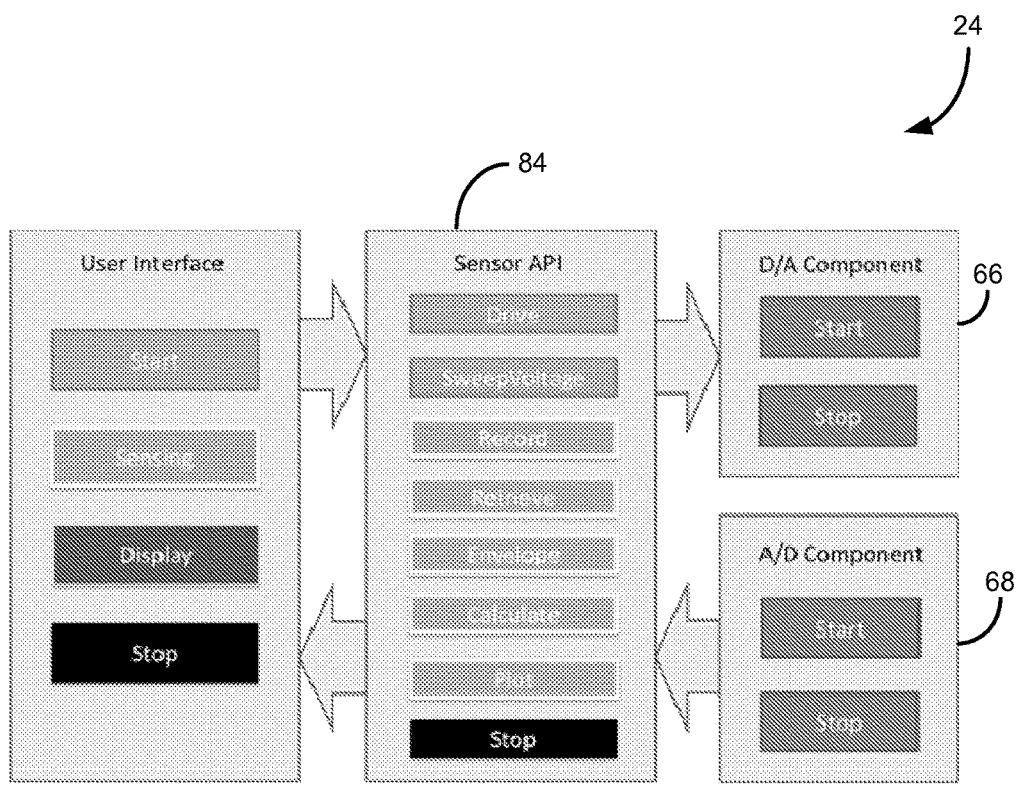
FIG. 4 is a block diagram of operations performed by the liquid sampling device and mobile device during operation, according to one implementation.

FIG. 4 provides additional details of one approach to implementing an operating method and the software application 80. There are digital-to-analog converter and analog-to-digital converter circuit components 66 and 68 in the testing circuit 24 that are leveraged in the method for use with corresponding circuit components of the mobile device 50 (not shown). A sensor application program interface module 84 includes functionality for selecting drive wave and sweep voltage parameters, controlling the sensor to record, retrieving data, selecting an appropriate envelope, performing calculations, plotting data, and stopping the current operation. The user interface, which is conveniently implemented as a touch interface on the mobile device 50, includes primary level functionality of starting and stopping operations, performing sensing functions, and displaying information, as indicated in the FIG. 4 implementation.

In operation, a user places a small liquid sample on the sensor 30. The user then initiates operation of the sensor, such as by pressing Start in FIG. 4. In the implementation of FIG. 2 and FIGS. 5a-5m, the user presses the Start Sensor button. The application 80 controls the liquid sampling device 10 to perform a test of the liquid sample.

Specifically, the audio circuit 54 of the mobile device 50 is controlled to generate a signal wave used to drive the testing circuit 24 with a selected sweeping voltage to perform the test with the sensor 30. Frequency matching between the mobile device circuit components and the testing circuit 24 is observed with appropriate use of the modulation and demodulation circuit components 62, 64. Data from the test is received from the circuit 24 by the audio circuit 54 and processed into digital form for display, storage and/or transmission.

In more detail, the audio circuit 54 includes a digital-to-analog converter and an analog-to-digital converter. The digital-to-analog converter generates the signal wave with the desired sweeping voltage to operate the sensor 30. In the implementation where the parameter of interest is nitrates, a reduction current and resultant output voltage representative of nitrate concentration in the sample are output from the sensor 30 and are received by the analog-to-digital converter of the audio circuit 54. The converted reduction current and voltage are compared with reference data, such as a stored calibration curve, thus allowing nitrate concentrations to be determined.

By name, the electrochemical method used to obtain the reduction/oxidation reaction is called cyclic voltammetry. Sodium hydroxide (NaOH) is used as an electrolyte and sodium nitrate with different concentrations is added to the electrolyte for testing. The electrodes are first activated by sweeping the potential from −1.4 V to 1.0 V for 50 cycles. This activation process will remove the possible oxidation layer at the surface of working electrode. To avoid oxidation of the silver working electrode and cause the nitrate reduction reaction to occur, the sweeping voltage between the working and reference electrodes is selected to be from 0 V to −1.4 V with a sweeping rate of 50 mV/s. The reduction peak of nitrate will be detected when sweeping toward −1.4 V.

There is generally a frequency limitation (which must be greater than 20Hz) for input and output signals from a mobile phone audio jack (such as the audio jack 52 and microphone). Accordingly, in one implementation, a sine wave at 1000 Hz with a triangular amplitude envelope increasing from 0 V to 1.4 V and decreasing from 1.4 V to 0 V, is selected for generation by the mobile device 50 and to be output via the audio jack 52 to drive the testing circuit 24. The demodulation circuit component 64 functions to detect the selected envelope. The cyclic sweeping voltage is then added to the reference potential and the working electrode is connected to ground, which results in the input voltage between the working and reference electrodes varying from 0 V to 1.4 V and then back to 0 V. Integrated operational amplifiers (not shown) are used in the testing circuit 24 as a potentiostat and transimpedance circuit to convert current to voltage. Since the frequency of this output voltage is low and under the 20 Hz limitation of the mobile device 50, and the amplitude is higher than the limitation for microphone input, the frequency modulation circuit component 62 converts the liquid sample test data to a signal within the allowed frequency range of the mobile device 50.

The raw data recorded by the mobile device 50 is a series of square waves at different frequencies from the frequency modulation circuit component 62 (such as, e.g. a CD4046 circuit) of the testing circuit 24. Therefore, the frequency of the windowed data is first averaged applied to obtain the frequency of the raw data. Then, a calibration method is used to transform the frequency values into actual voltage values. The sampling rate of the mobile device is 32000 bytes/s, and each voltage value is stored as a short integer, so 16000 data points are recorded each second. The output from the FM integrated circuit is a square wave with an amplitude larger than 0.7 V, but the input/output to the audio circuit 54 of the mobile device 50 is limited to 200 mV. Hence, the recorded wave is a truncated square wave with maximum and minimum values of 32767 and −32767, respectively. The frequency value is calculated by counting the number of steps from maximum to minimum by setting 1600 samples as one period. Calibration is performed to convert the output frequency from the frequency modulation integrated circuit into voltage, and finally to oxidation-reduction current using trans-impedance circuit.

Nitrate reduction in alkaline media is either a two-electron (94%) or eight-electron (6%) process as given below:

$$NO_3^- + H_2O + 2e^- \rightarrow NO_2^- + 2OH^-$$

$$NO_3^- + 6H_2O + 8e^- \rightarrow NH_3 + 9OH^-$$

Figure 7:
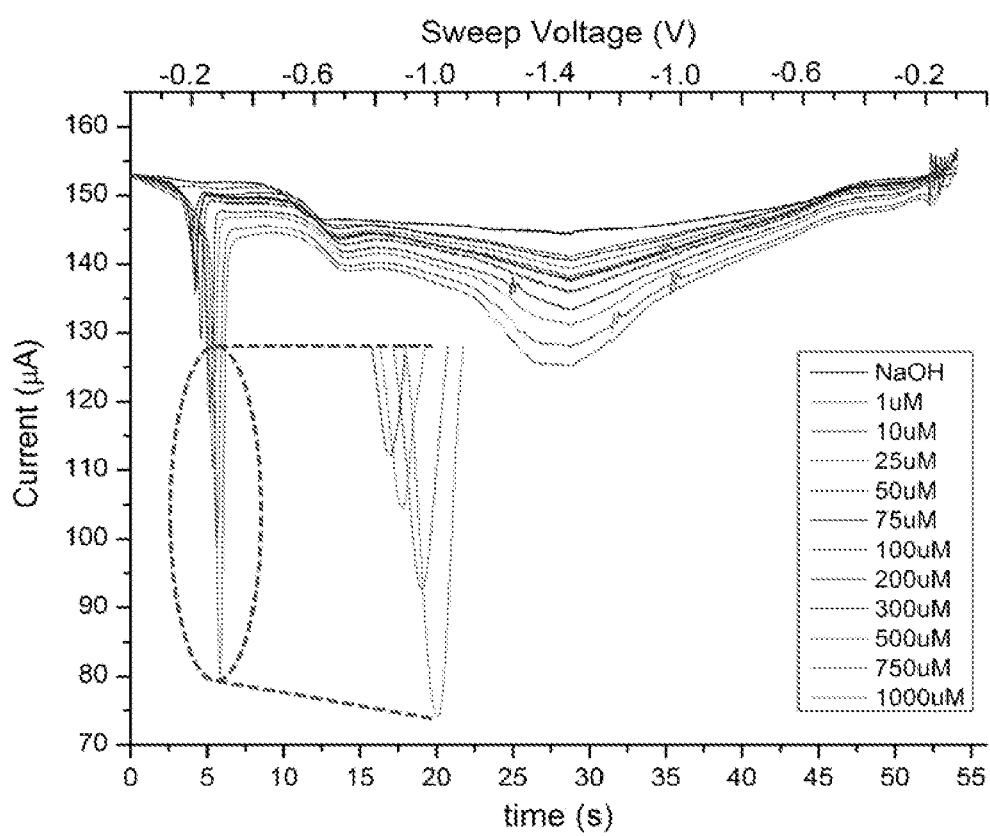
FIG. 7 is a graph of representative nitrate concentration test results measured over varying sweep voltage and time.

During the forward sweeping process (0 V to −1.4 V), there are current peaks which occur at around −0.2~−0.3V (see dashed ellipse in FIG. 7). These current peaks are also dependent on the concentration of nitrate present in the solution. Sodium nitrate solutions at different concentrations (1 μM to 1 mM) with 0.1 M NaOH electrolyte medium are tested using the liquid sampling device 10 and attached mobile device 50. FIG. 7 shows representative testing results changing with time and sweeping voltage. The peaks at −0.6 V can be attributed to hydroxide desorption process on the silver electrode. In the anodic sweeping process, a small anodic current peak occurs at around −0.42V, which is due to the electro-chemisorption of hydroxide ions.

Figure 8A:
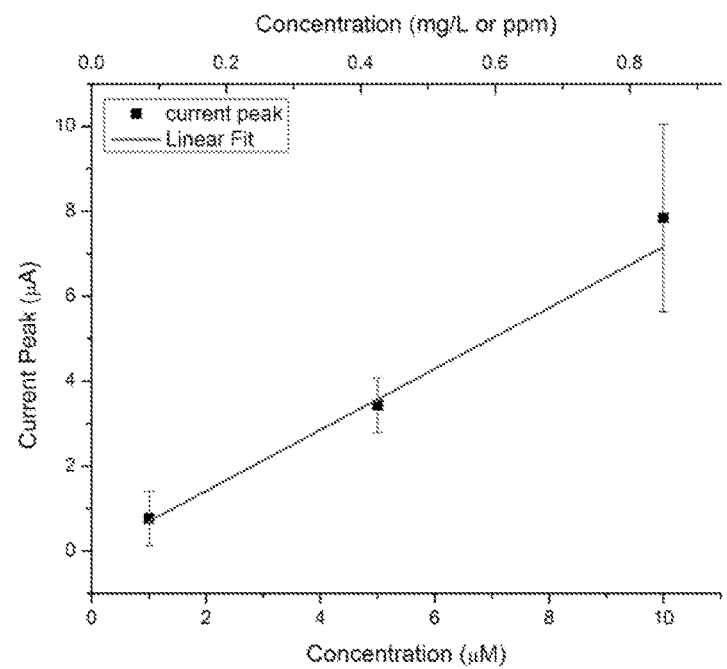
FIGS. 8A, 8B and 8C are graphs of calibration curves showing concentration versus current over three different concentration ranges: about 1 µM~10 µM, about 10 µM~200 µM and about 200 µM~1000 µM.
Figure 8B:
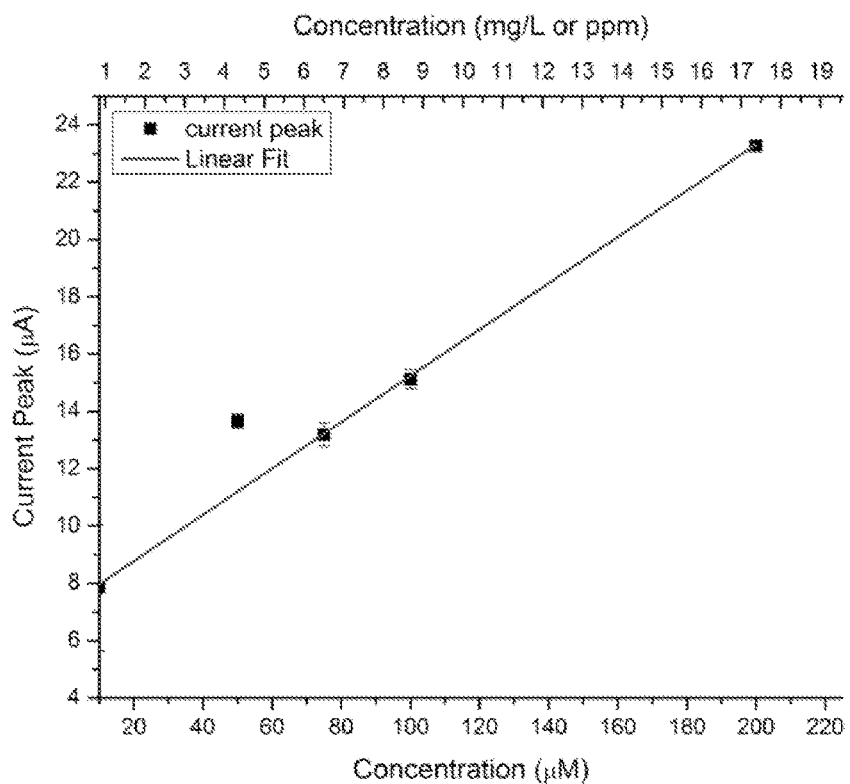
Figure 8C:
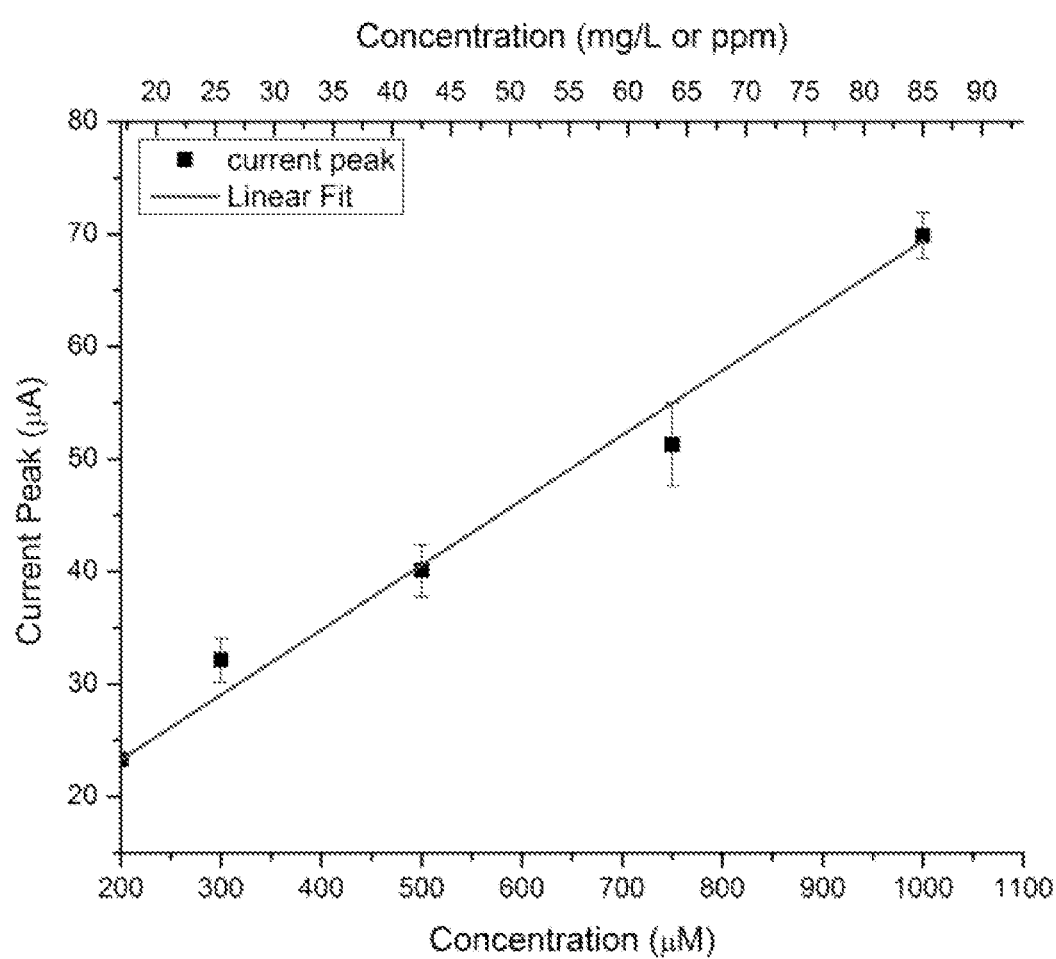

Referring to FIGS. 8a, 8b and 8c, a calibration curve is obtained from the current reduction peak values after data processing. The identification of reduction peaks should take into account the following three points. First, the drift in the bias potential applied to the sensor 30 due to battery consumption. The drift changes about 0.1 mV for each testing cycle (56 s). Second, there is a small drift in the reference potential with time. Although silver as a reference electrode material shows substantially stable potential, there is still drift of about 25 mV over 10 h for a silver electrode in 0.01 M NaOH electrolyte solution. Third, the electrolyte, sodium hydroxide, has its own reduction peak in the sweeping voltage ranges of the system, which is manifested as background current in each test. In order to correct for all three above factors, the current reduction peaks are first obtained by calculating the difference between peak and valley values around −0.2V~−0.3V on each curve. This process will remove the effect of battery potential drift and reference silver electrode potential drift. Then, a background NaOH current value is subtracted from these peak values to minimize perturbation from electrolyte. The resulting calibration curve can be defined over three ranges for greater accuracy as shown in the figures. In each of the three ranges, the peak current has a linear relationship to nitrate concentration. The application 80, which is described in more detail below, can include a module to conduct calibration tests and store calibration data.

EXAMPLE

Figure 9A:
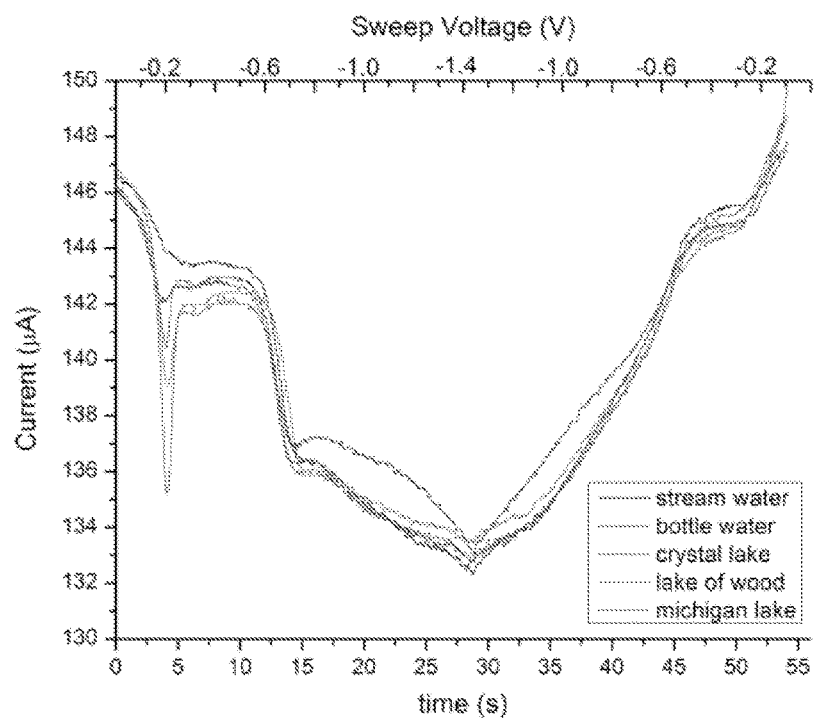
FIG. 9A is a graph of the liquid sample test results for five different sources of water.
Figure 9B:
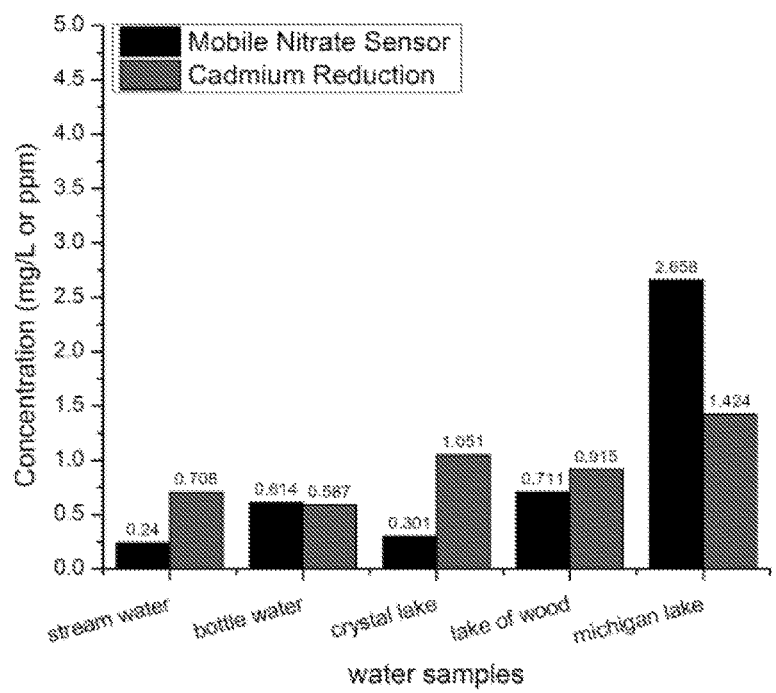
FIG. 9B is a bar graph comparing the nitrate concentrations for the five samples as determined by the liquid sampling device ("mobile nitrate sensor") and a comparison method.

The nitrate sensor 30 of the liquid sampling device 10 as controlled by the mobile device 50 was used for measuring nitrate concentration in real water samples. FIG. 9a shows the results of different water samples, including water from a stream ("stream water"), bottled water ("bottle water"), water from Crystal Lake ("crystal lake"), water from Lake of the Woods ("lake of wood") and water from Lake Michigan ("Michigan Lake"). Current peaks appear near −0.2~−0.3V. The raw data was processed to remove the effect of background change and bias voltage drift as described above. To verify the accuracy of these measured results, the "gold standard" cadmium reduction method was performed to make a comparison. The cadmium reduction method is based on the reduction of nitrate to nitrite on cadmium as a catalyst, followed by Griess reaction to form a fluorescent chemical. The comparison of nitrate concentration of different water samples after calibration using the two different methods is shown in FIG. 9b.

From the results, the lowest and highest concentrations of nitrate ion are found in the stream water sample and the Lake Michigan water sample, respectively. This tendency is consistent for both the described method (the "mobile nitrate sensor" approach) and the cadmium reduction method. Accordingly, the described method is shows good qualitative and quantitative agreement with the cadmium reduction method.

The software application 80 can be implemented to operate with various operating systems of current mobile devices. For example, in FIG. 1c, the application 80 is implemented on a Samsung mobile phone with Windows Phone 7.5 OS. As indicated in FIG. 4, the application 80 can incorporate a Sensor API provided by Microsoft having certain functions that can be called by user commands. At the left of FIG. 4, four basic functions of one representative user interface are shown. The Start function provides a sweeping voltage to drive the sensor 30 (with options to change the waveform and other parameters as described below). The Sensing function is mainly used to retrieve data from the output of the sensor 30, and to analyze data, including the steps of initiating FM demodulation, down sampling and calibration. The Display function is used for plotting the results for visualization and display.

Figure 5A:
FIGS. 5A-5I are representative mobile device screen displays showing various capabilities of a mobile device application for interfacing with the liquid sampling device, according to one implementation.
Figure 5B:
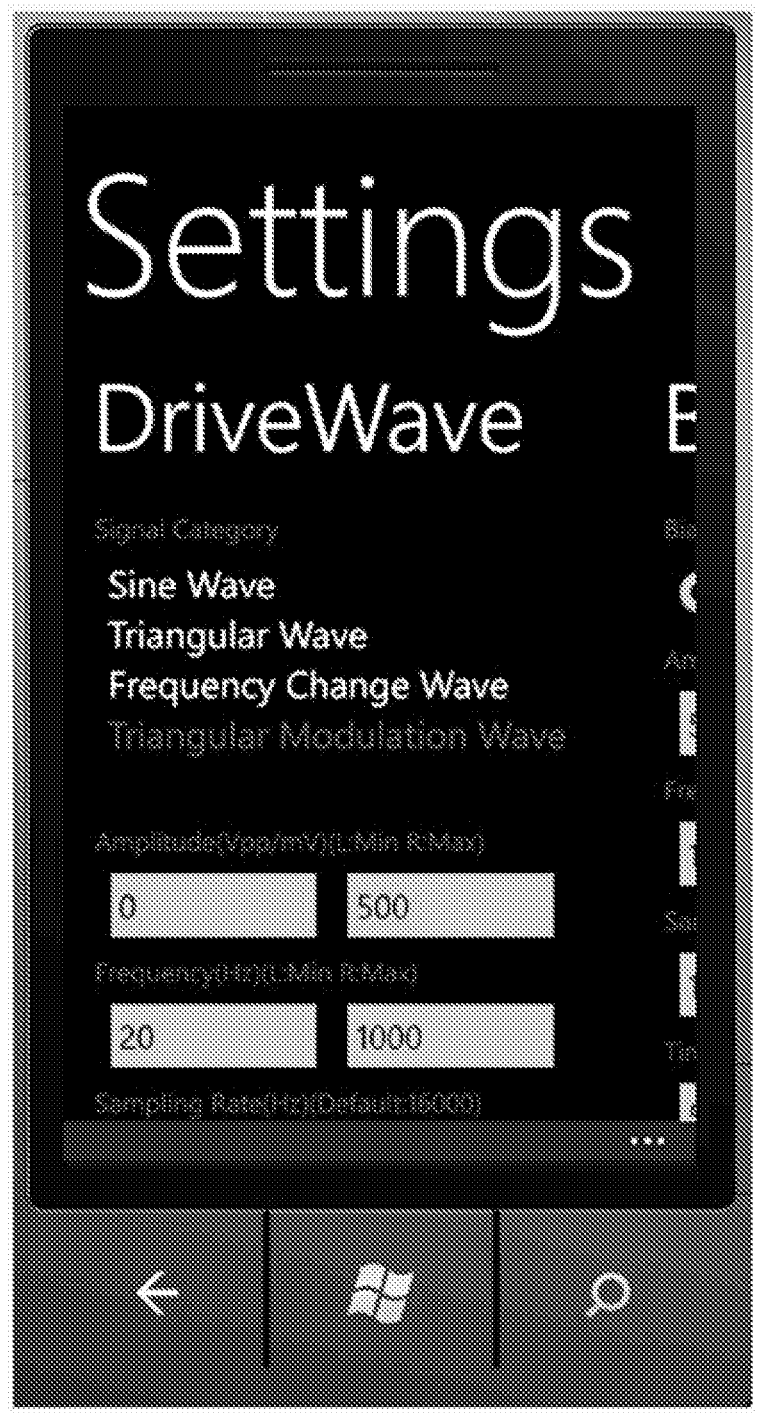
Figure 5C:
Figure 5D:

FIGS. 5a-5i illustrate screen displays from another implementation of the application 80. In FIG. 5a, a main screen for an application MoboSens is shown. The application has touch-sensitive area corresponding to functions for Start Sensor, Parameters, View Map, Weather and Settings. As shown in FIG. 5b, the Settings function allows the type of signal wave to be selected, and its amplitude frequency and sampling rate can also be modified. In FIG. 5c, the bias voltage can be set (including amplitude, frequency, sampling rate and number of times parameters). In FIG. 5d, the down sampling rate can be set.

Figure 5E:
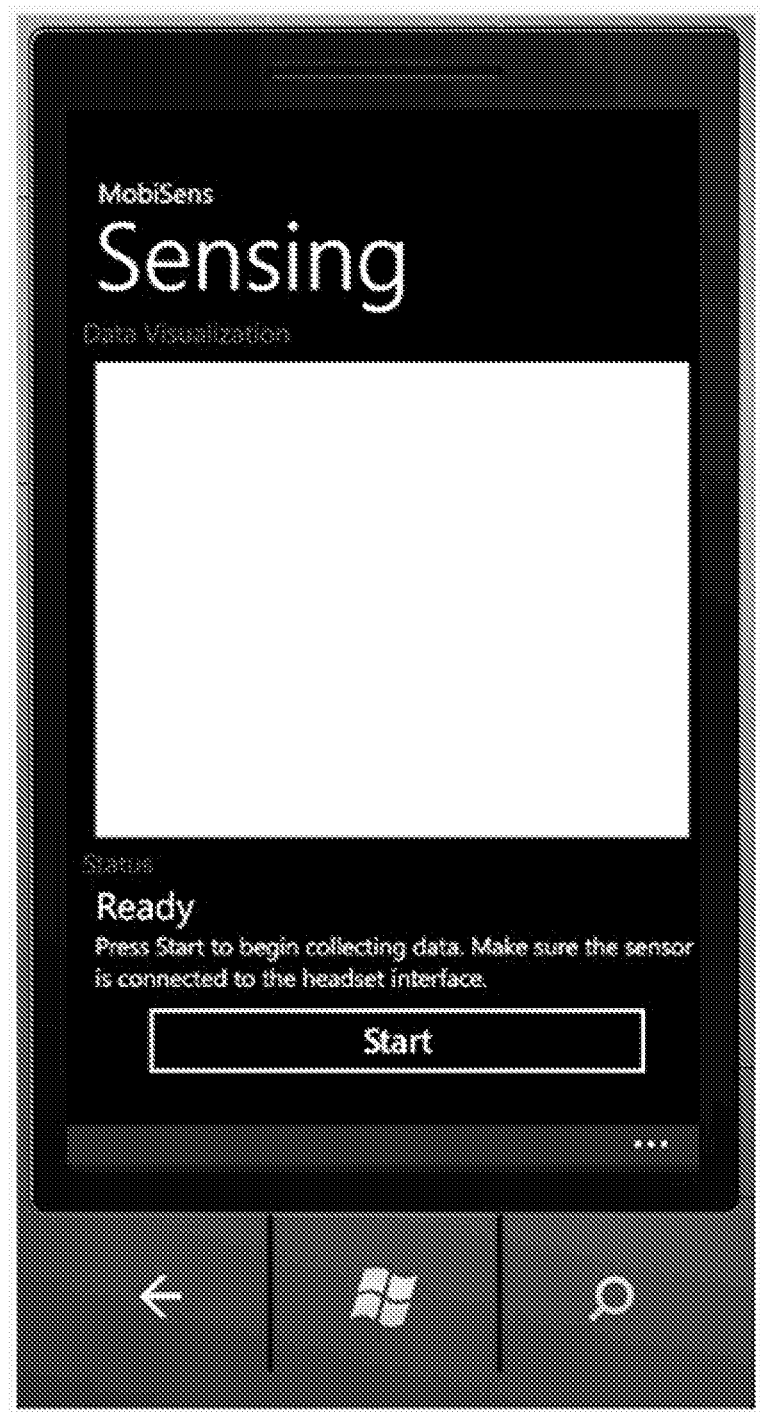

In FIG. 5e, the user can control when to begin testing of the liquid sample (or sensing) with the liquid sampling device 10. Specifically, the user is provided with instructions for ensuring that the liquid sampling unit 10 is properly connected to the mobile device 50, and is prompted to press a Start button when the testing should be begun. In a Data Visualization section, a graph corresponding to the current test will be displayed.

Figure 5F:
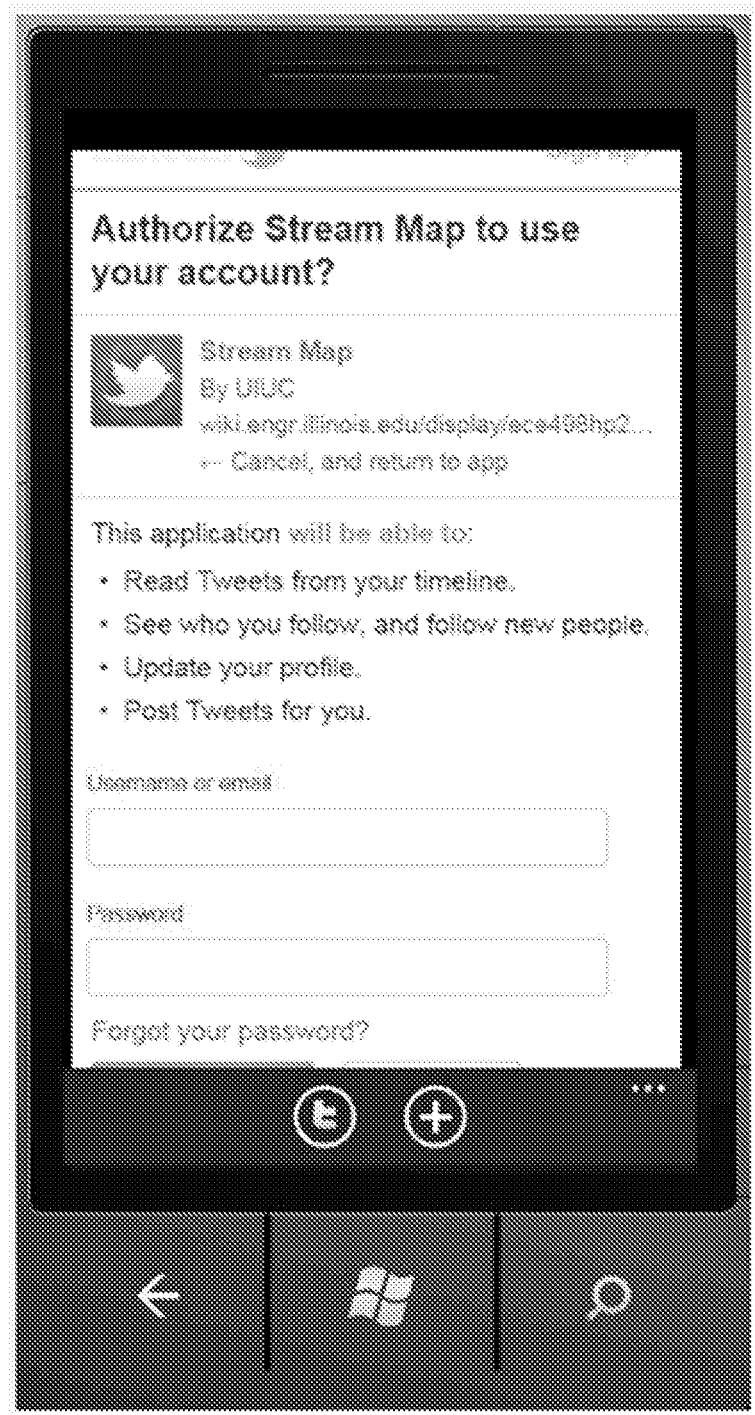
Figure 5G:
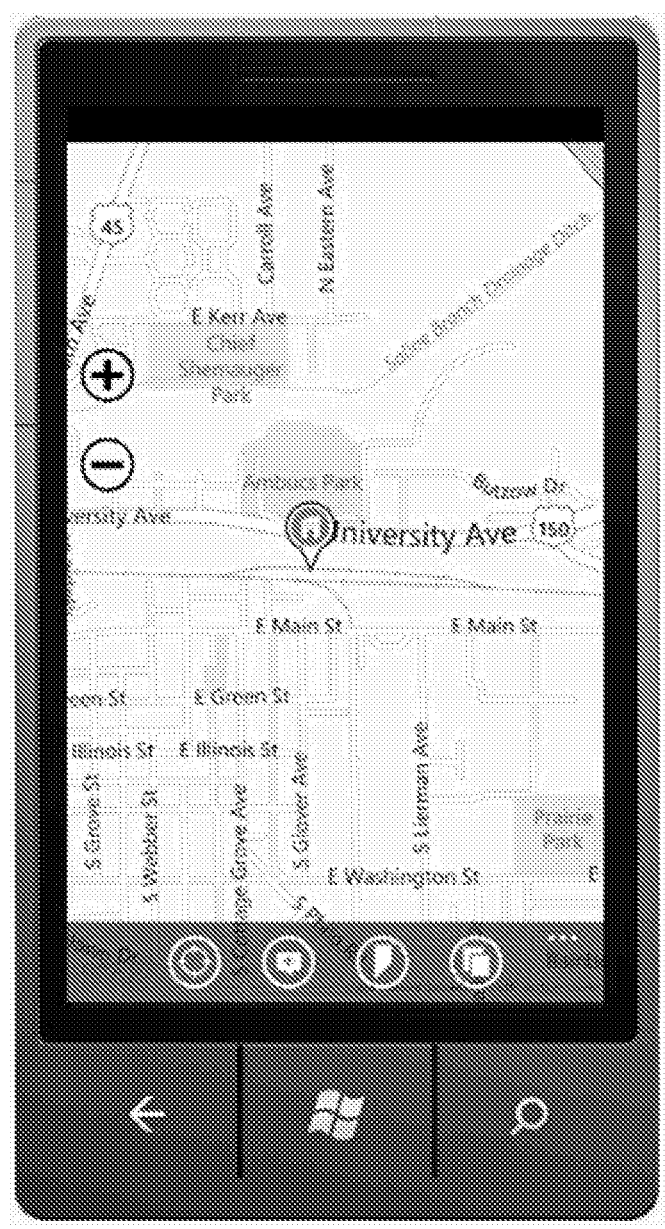
Figure 5H:
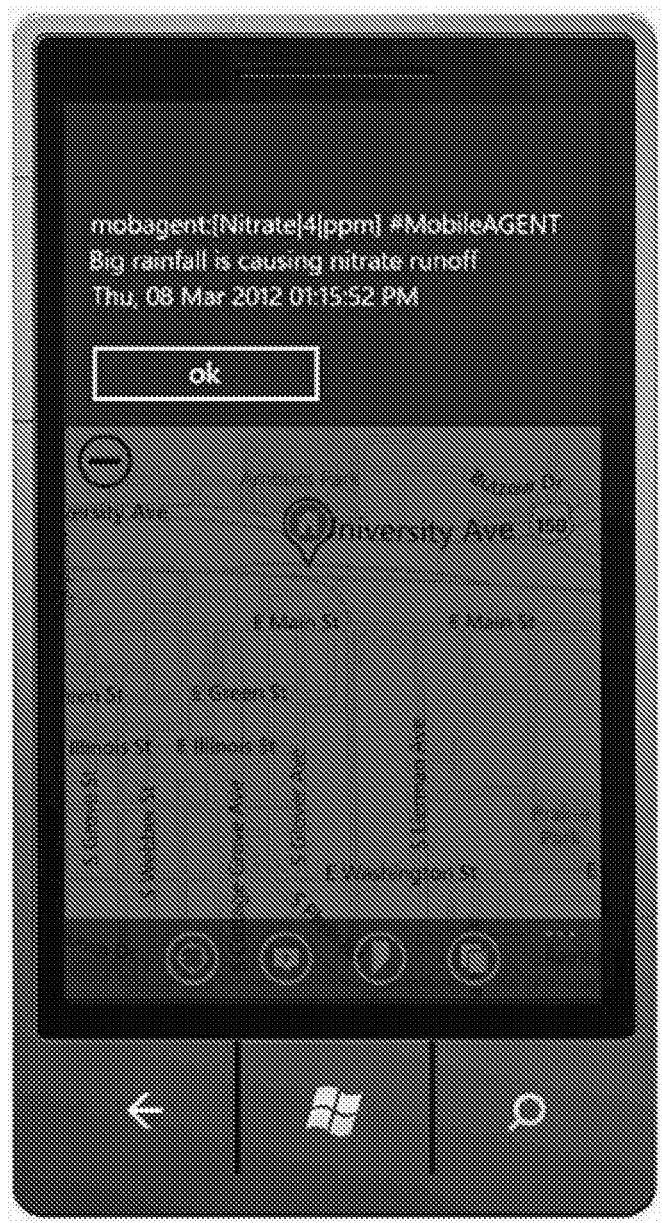
Figure 5I:

In FIG. 5f, the user is prompted to enter her identifying username and password. The application can be set to require such credentials for any use generally, or only if use requires other applications (such as Twitter in this example). In FIG. 5g, the user has selected View Map to show the current location of the mobile device and conveniently, the just completed test result on a map of the area. FIG. 5h is a screen display showing that the user plans to post the test result, e.g., to a network, with a comment that she added, "Big rainfall is causing nitrogen runoff." FIG. 5i is a screen display allowing the user to send data. As indicated, other types of data may include data on radioactivity and/or data on oil spills.

Figure 6A:
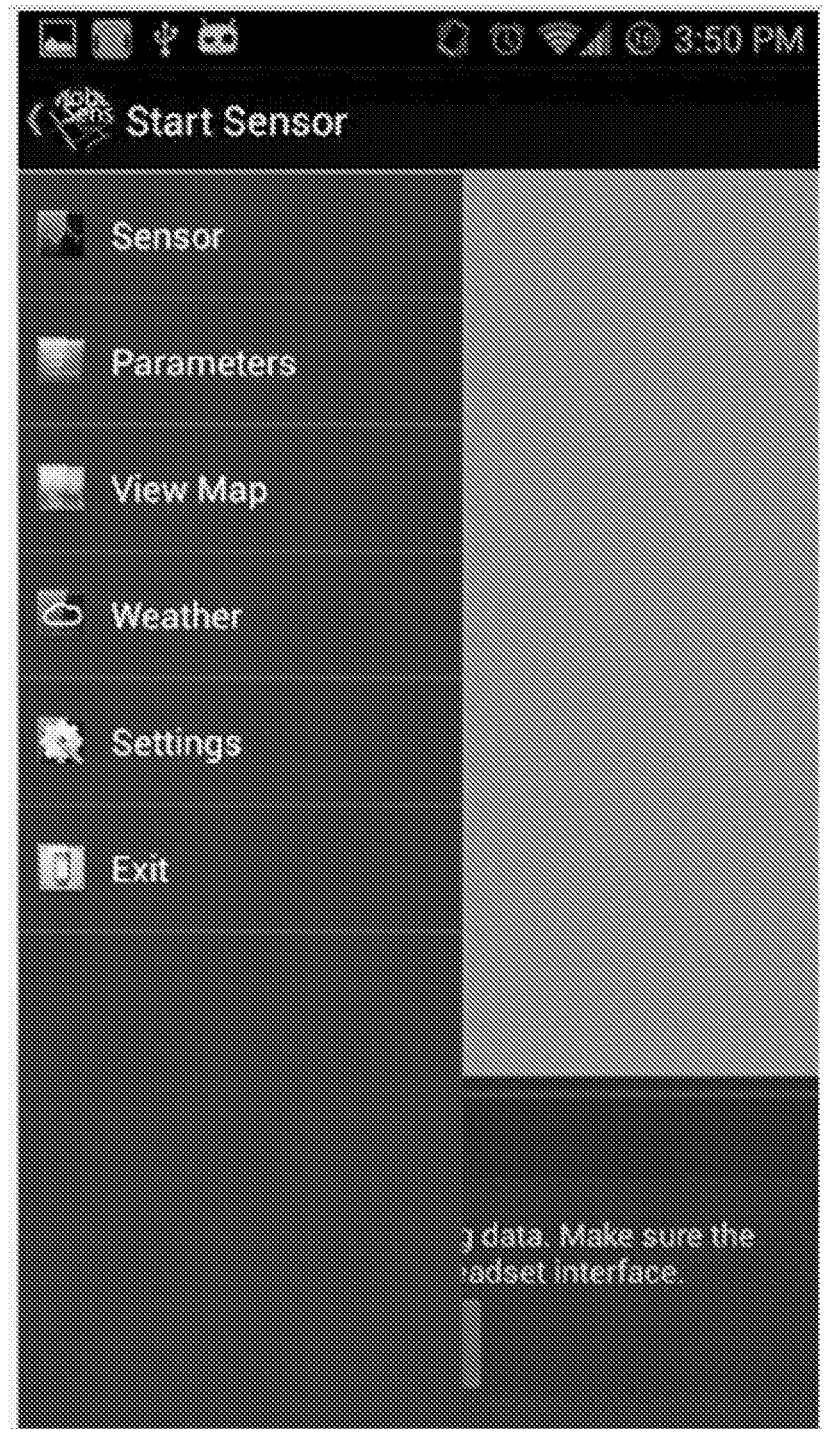
FIGS. 6A-6F are representative mobile device screen displays showing a mobile device application for interfacing with the liquid sampling device according to another implementation.
Figure 6B:
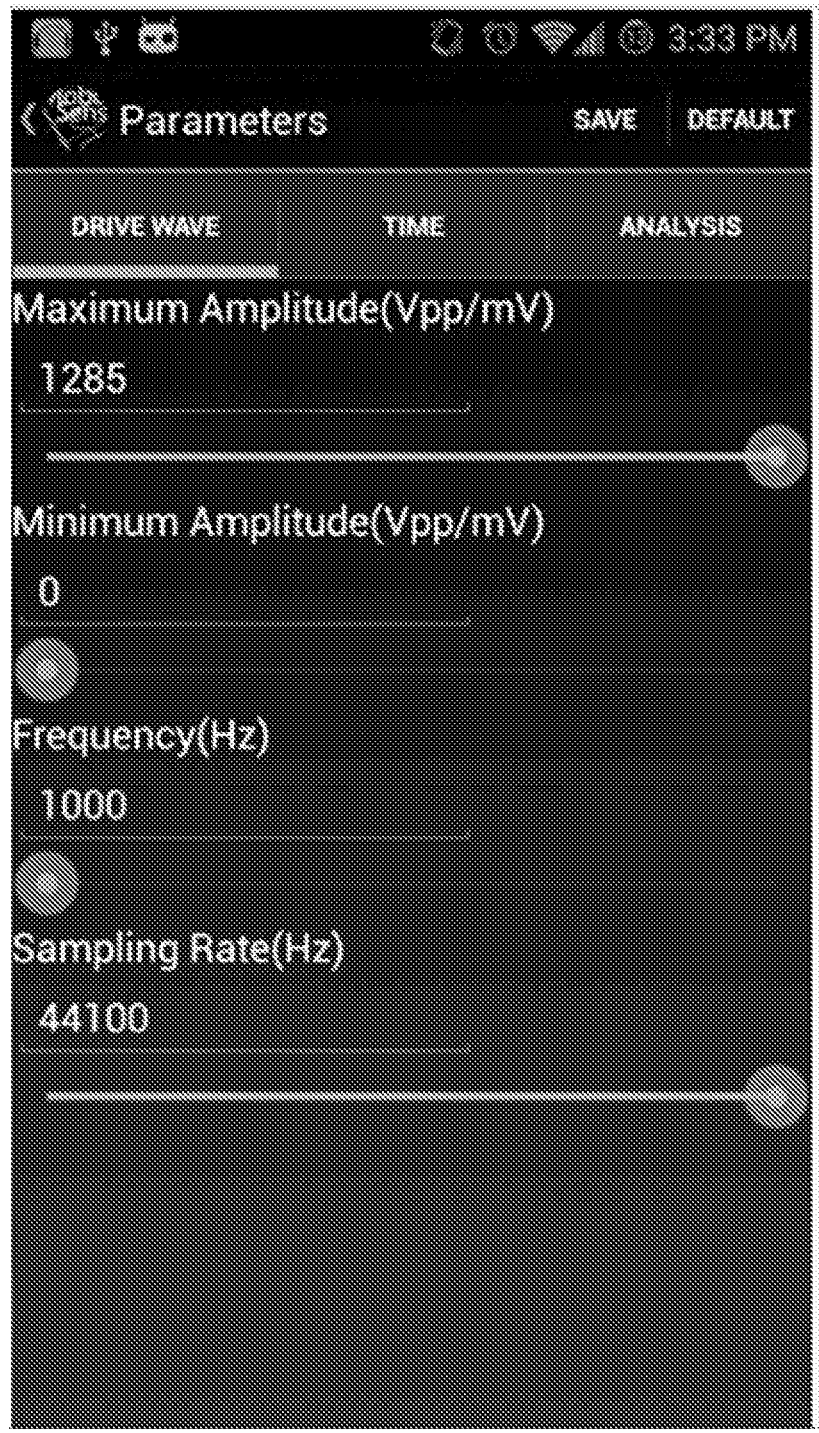
Figure 6C:
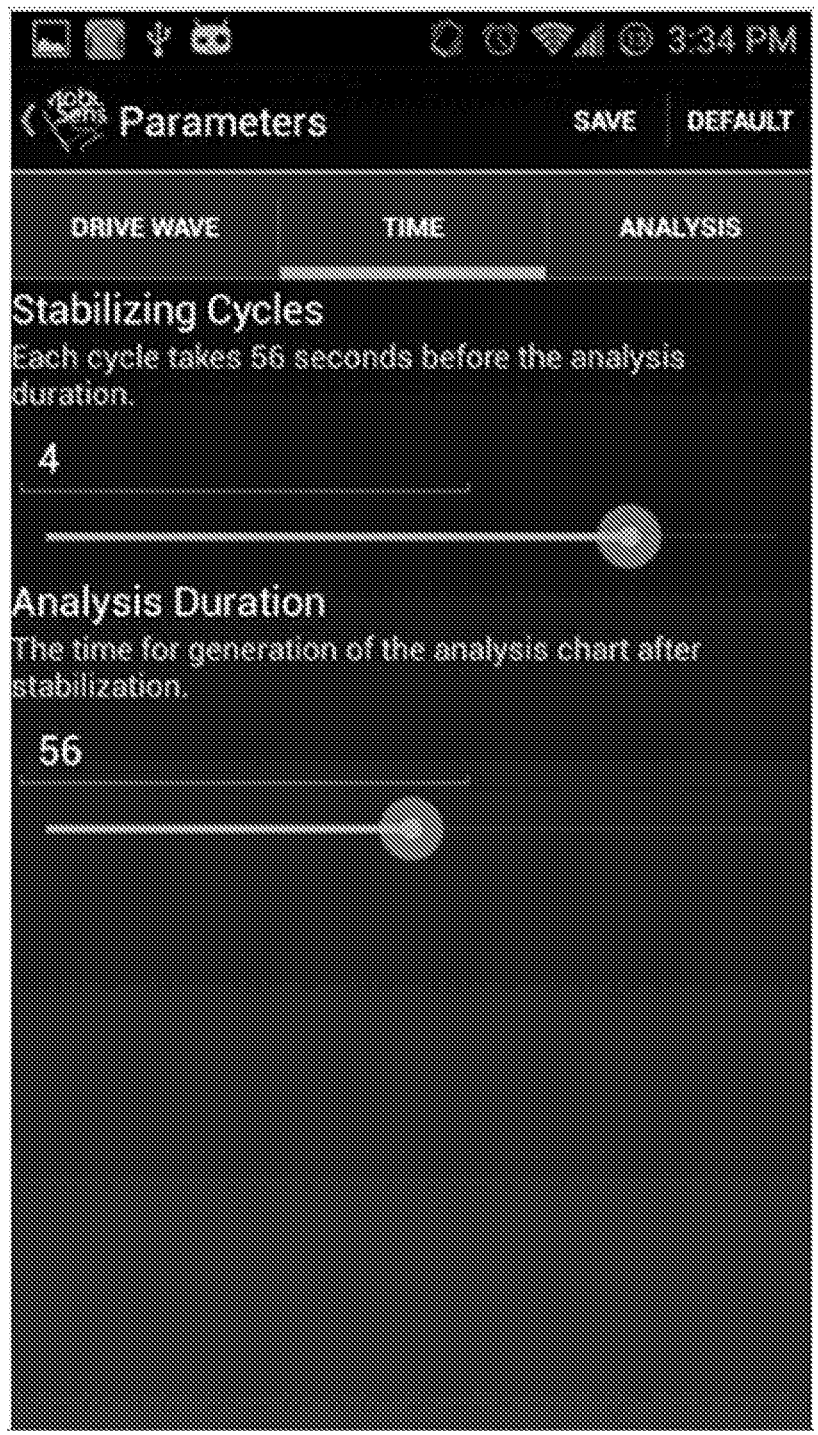
Figure 6D:
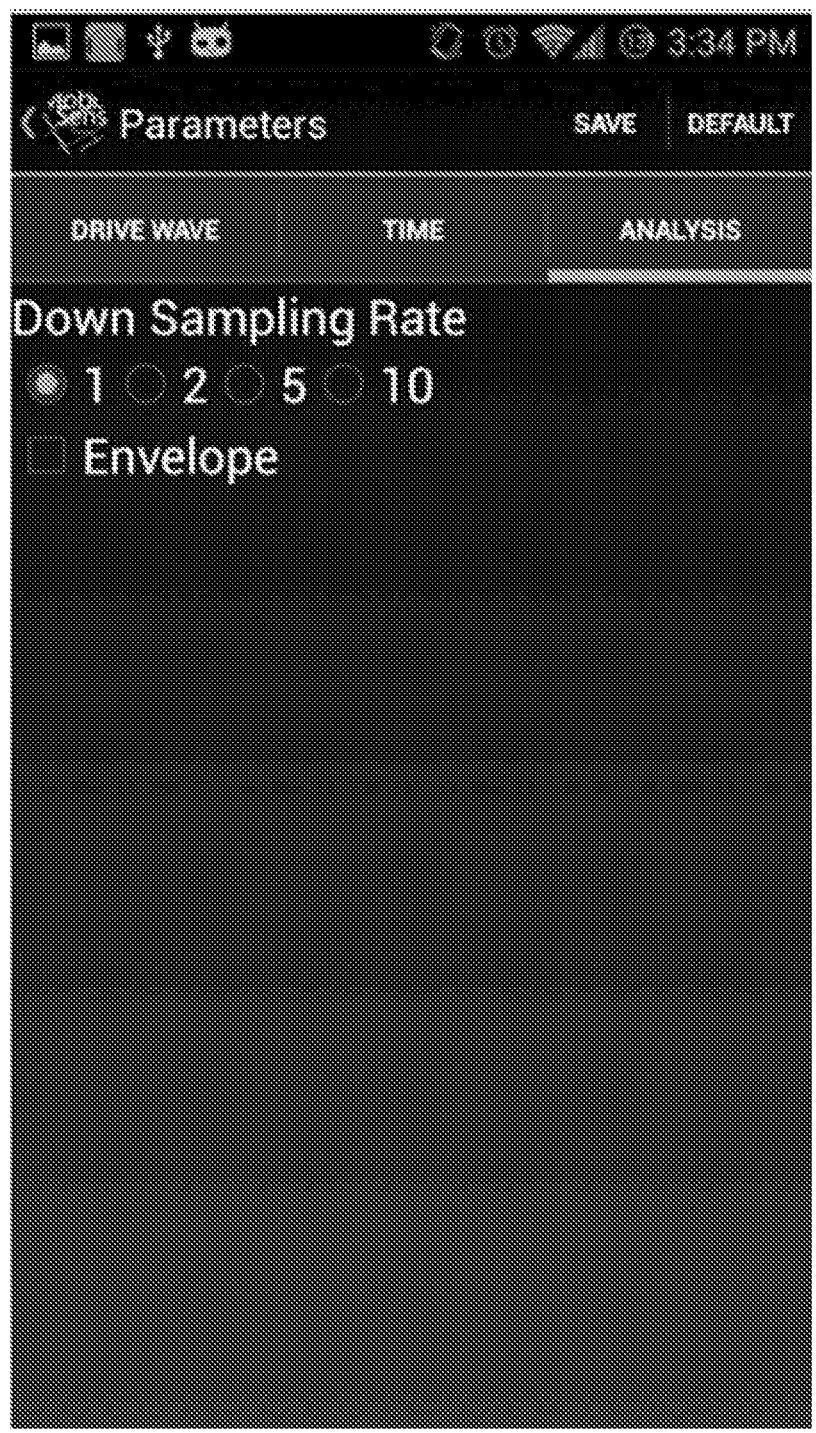
Figure 6E:
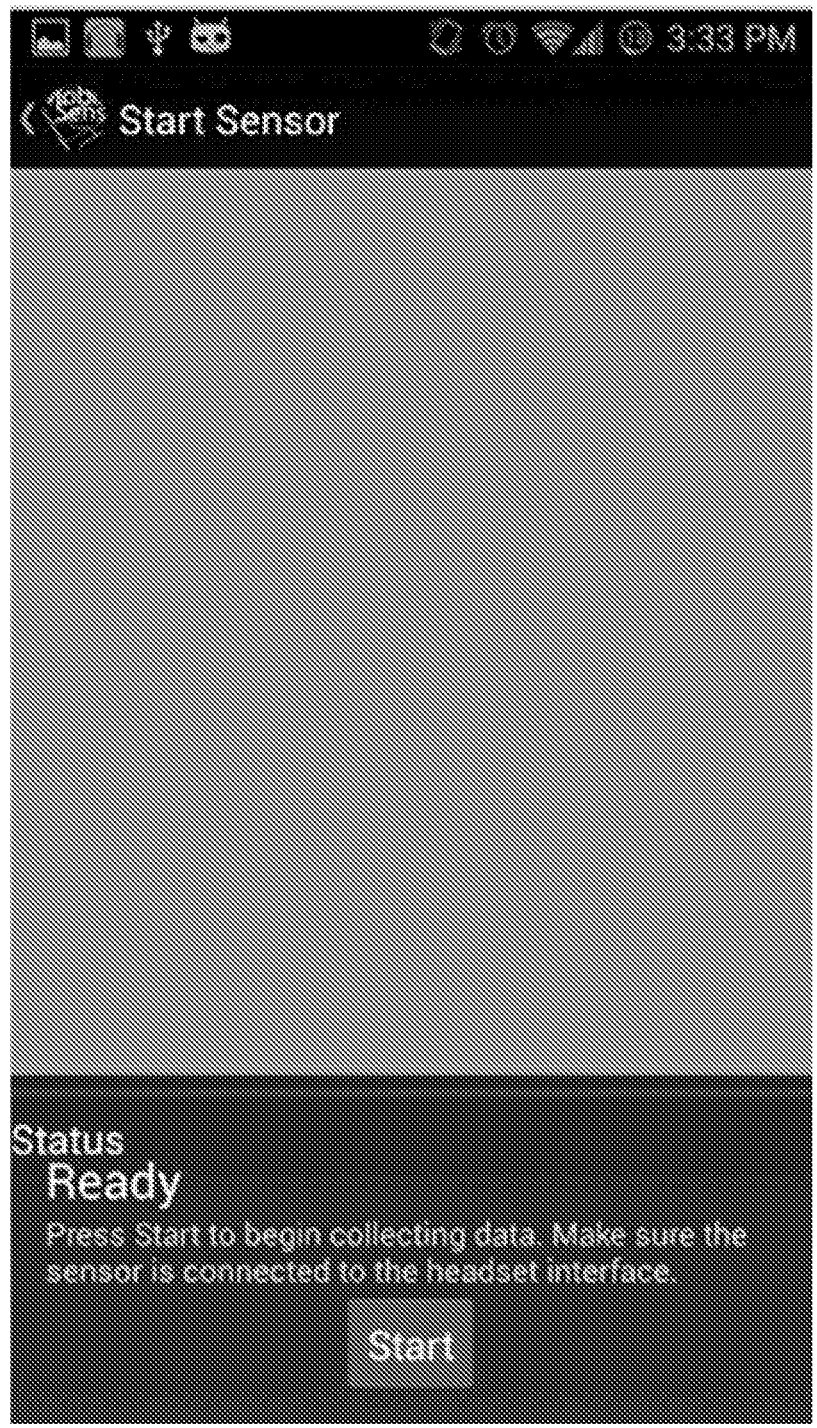
Figure 6F:
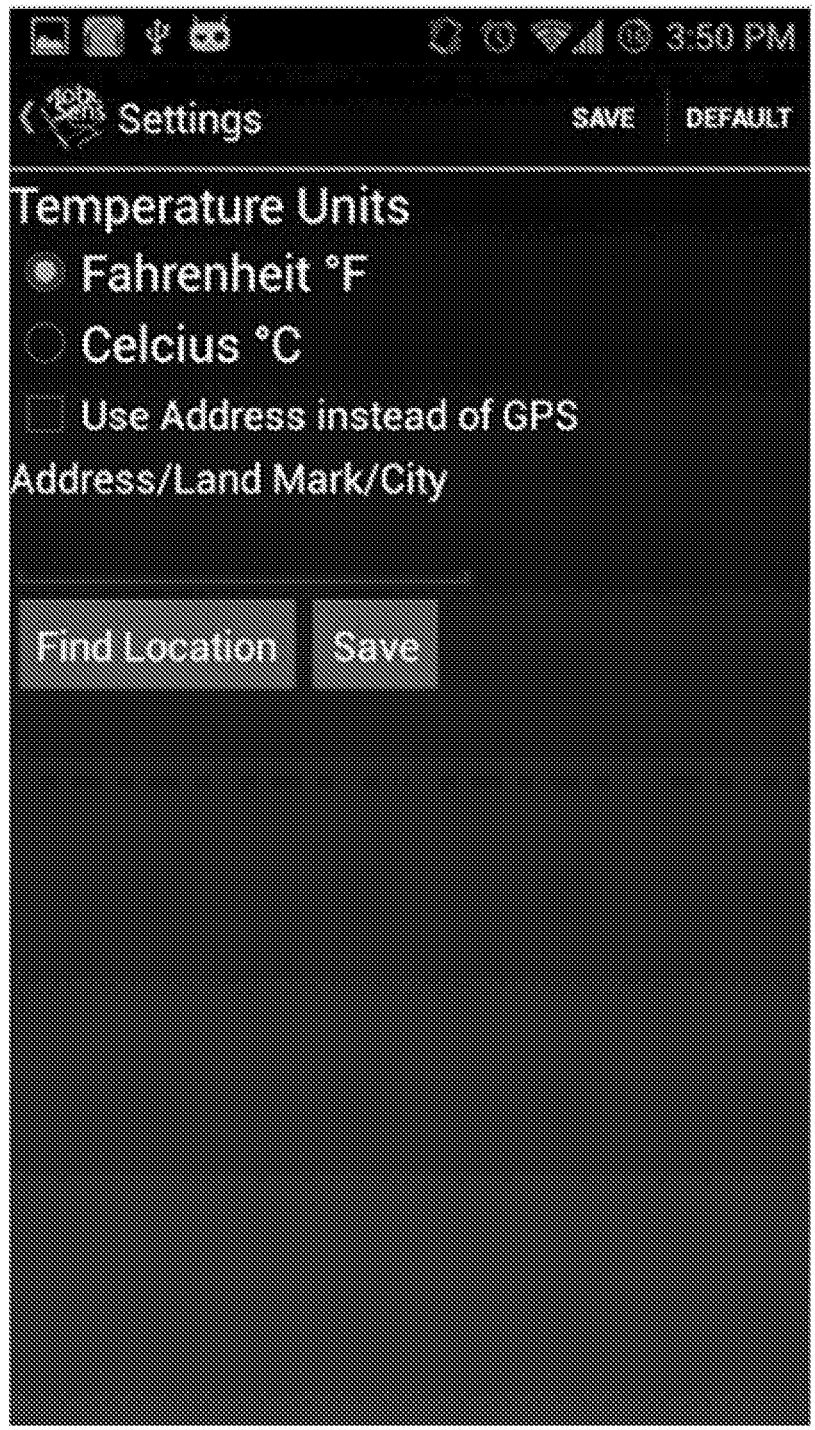

FIGS. 6a-6f illustrate representative screen displays for yet another implementation of the application 80, which is very similar to the implementations described above, except for minor differences. FIG. 6a shows the main screen. FIGS. 6b, 6c and 6d show screen displays for receiving commands to change parameters for the drive wave, sample testing time and sample analysis, respectively. FIG. 6e is the "Start Sensor" screen, which generally corresponds to the screen shown in FIG. 5e. FIG. 6f is a settings screen relating to temperature units and how locations are specified.

As illustrated, the test results for nitrate concentration in real water samples can be stored and shared. The test results can be shared on internet social networks like Twitter or uploaded to remote servers (public or private), e.g. in a cloud database, for further data analysis. Test results can be linked geospatial locations (latitude and longitude) indicating the source of the sample, temperature and/or user inputs and observations (i.e., metadata). Desirably, the application 80 provides for an integrated view of test results on a map, such as using Google maps or another similar service. The sensor types and temperature data may also be included in the posted data.

Figures 3A, 3B, 3C:
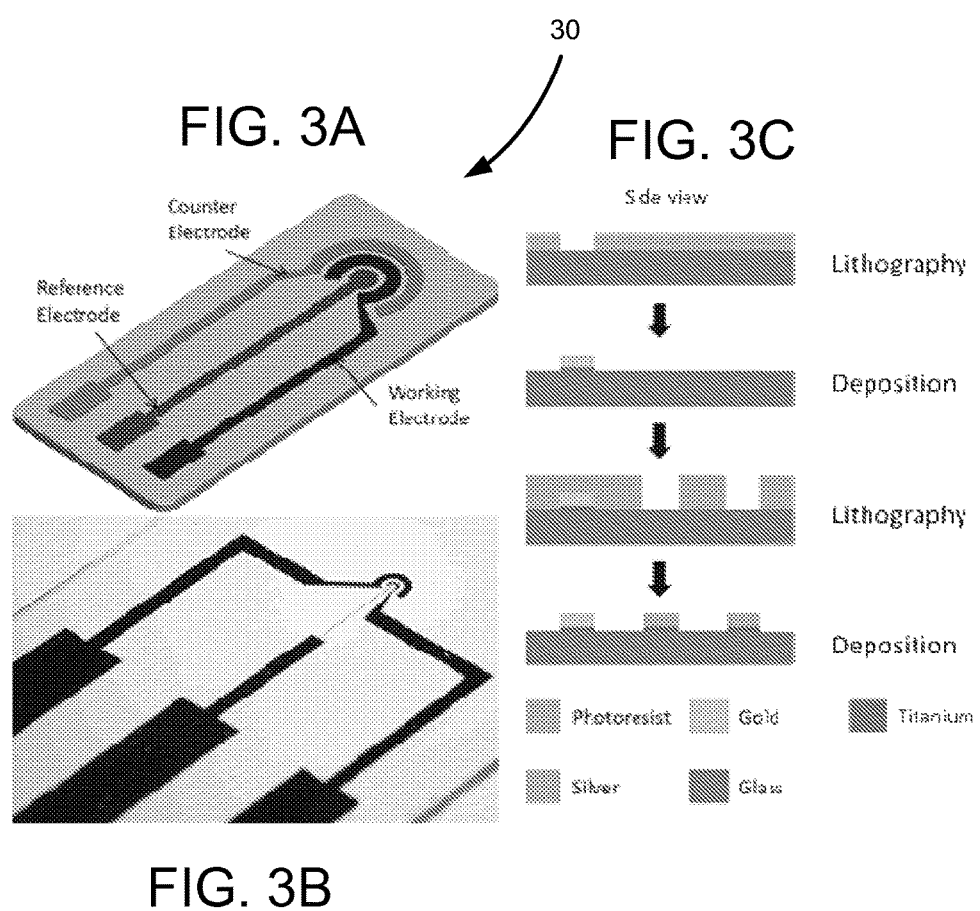
FIG. 3A is a perspective view of the sensor of the liquid sampling device.
FIG. 3B is a magnified view of a portion of the sensor.
FIG. 3C is a schematic view showing a sequence of representative steps involved in fabricating the sensor.

Referring to FIGS. 3a, 3b and 3c, details of the fabrication of the sensor 30 are shown. The sensor 30 is fabricated on a glass substrate 32 and comprises a working electrode 34, a counter electrode 36 and a reference electrode 38 positioned between the working and counter electrodes 34, 36. A representative layout of the sensor is shown in FIG. 3a, and a magnified image of a portion of a corresponding sensor is shown in FIG. 3b. The electrodes 34, 36 and 38 are laid out in a circular fashion to enable uniformity in the current flow in the electrochemical system. In the illustrated implementation, the surface areas of the counter electrode 36, the working electrode 34 and the reference electrode 38 are $9.05 \times 10^{-4} cm^2$, $7.05 \times 10^{-4} cm^2$ and $3.47 \times 10^{-4} cm^2$, respectively. The area of the counter electrode 36 is designed to be largest for preventing oxygen-bubble formation on its surface due to $OH^-$ oxidation at high current density.

A schematic illustration of a representative fabrication process is shown in FIG. 3c. The counter electrode is first patterned by optical lithography, and a 200 nm gold layer is deposited by electron beam (e-beam) evaporation. After removal with acetone, the gold inside the counter electrode region will remain. Using the same method, another layer of silver (200 nm) is provided for the reference and working electrodes. Ag/AgCl is usually used as the reference electrode, but it may also produce chloride contamination during nitrate detection. Instead, silver is used as reference electrode due to its simplicity in fabrication and sufficiently stable potential in 0.01M NaOH electrolytes. It has been reported that silver has high sensitivity for reducing nitrate ions, so silver is implemented as the material of the working electrode in this example. For better adhesion on glass, one layer of titanium (20 nm) instead of chromium was deposited before gold and silver evaporation because the chromium adhesion layer severely corroded during the electrochemical activation process. In order to minimize potential drop between reference and working electrodes, these two electrodes are kept as close as 10 µm to increase accuracy.

In the implementations above, the liquid sampling device 10 is configured to be small for portability and easy handling. For portability, a small circuit "box" or receiving space sized for the testing circuit 24 was made with a light fixture frame fabricated using rapid prototyping manufacturing process. The fixture frame provides stability to the overall configuration when the liquid sampling device 10 is attached to the mobile device 50. Easy handling is achieved by using a micro-fluidic structure (not shown), which is made of PDMS. The sensing electrodes are covered by a small chamber in the micro-fluidic structure. The user need only drop a liquid sample at the tip of the structure and it will be drawn into the chamber thereof by capillary action to allow testing to take place.

Figure 10:
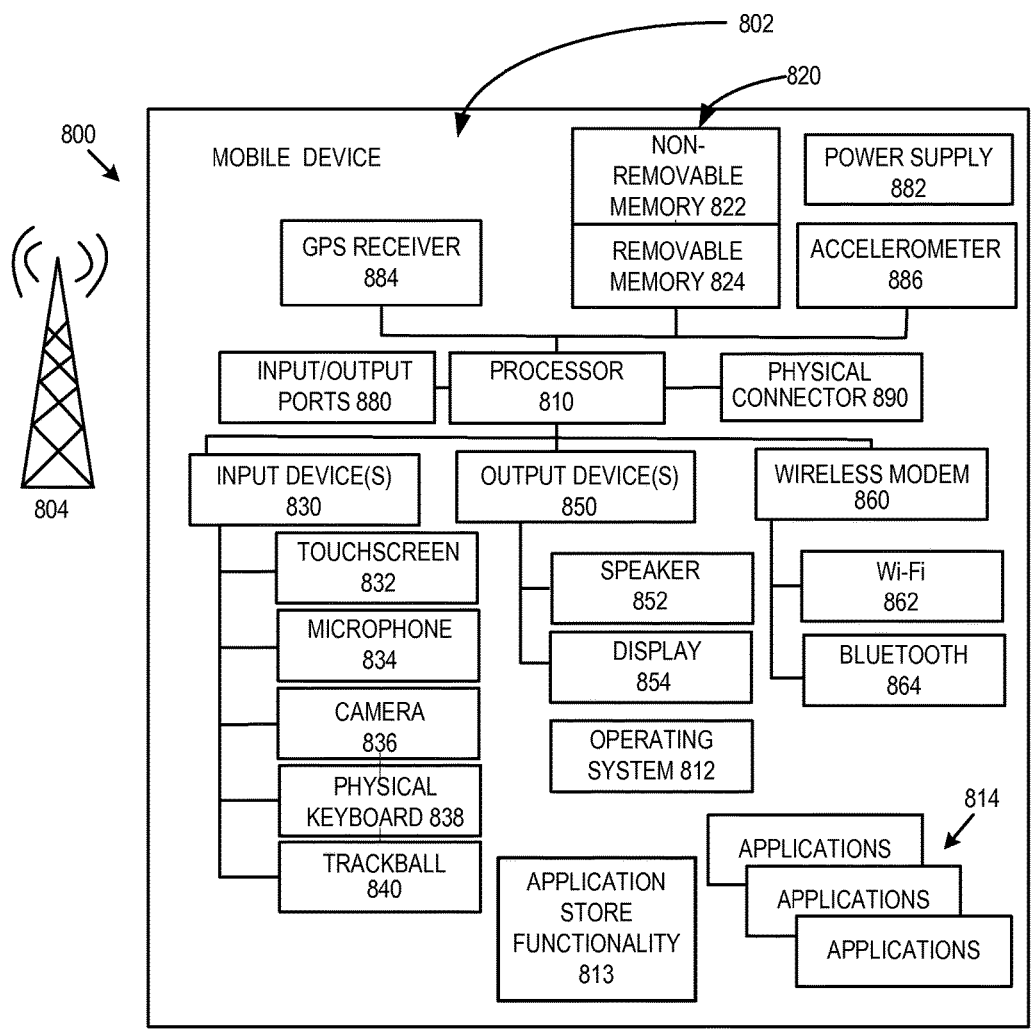
FIG. 10 is a system diagram of an exemplary mobile device.

FIG. 10 is a system diagram depicting another exemplary mobile device 800 including a variety of optional hardware and software components, shown generally at 802. Any components 802 in the mobile device can communicate with any other component, although not all connections are shown, for ease of illustration. The mobile device can be any of a variety of computing devices (e.g., cell phone, smartphone, tablet, handheld computer, Personal Digital Assistant (PDA), etc.) and can allow wireless two-way communications with one or more mobile communications networks 804, such as a cellular or satellite network.

The illustrated mobile device 800 can include a controller or processor 810 (e.g., signal processor, microprocessor, ASIC, or other control and processing logic circuitry) for performing such tasks as signal coding, data processing, input/output processing, power control, and/or other functions. An operating system 812 can control the allocation and usage of the components 802 and support for one or more application programs 814 ("applications"). The application programs can include common mobile computing applications (e.g., email applications, calendars, contact managers, web browsers, messaging applications), or any other computing application, such as the application 80 described above. Functionality 813 for accessing an application store can also be used for acquiring and updating applications 814.

The illustrated mobile device 800 can include memory 720. Memory 820 can include non-removable memory 822 and/or removable memory 824. The non-removable memory 822 can include RAM, ROM, flash memory, a hard disk, or other well-known memory storage technologies. The removable memory 824 can include flash memory or a Subscriber Identity Module (SIM) card, which is well known in GSM communication systems, or other well-known memory storage technologies, such as "smart cards." The memory 820 can be used for storing data and/or code for running the operating system 812 and the applications 814. Example data can include web pages, text, images, sound files, video data, or other data sets to be sent to and/or received from one or more network servers or other devices via one or more wired or wireless networks. The memory 820 can be used to store a subscriber identifier, such as an International Mobile Subscriber Identity (IMSI), and an equipment identifier, such as an International Mobile Equipment Identifier (IMEI), which are transmitted to a network server to identify users and equipment.

The mobile device 800 can support one or more input devices 830, such as a touchscreen 832, microphone 834, camera 836, physical keyboard 838 and/or trackball 840 and one or more output devices 850, such as a speaker 852 and a display 854. Other possible output devices (not shown) can include piezoelectric or other haptic output devices. Some devices can serve more than one input/output function. For example, touchscreen 832 and display 854 can be combined in a single input/output device. The input devices 830 can include a Natural User Interface (NUI). An NUI is any interface technology that enables a user to interact with a device in a "natural" manner, free from artificial constraints imposed by input devices such as mice, keyboards, remote controls, and the like. Examples of NUI methods include those relying on speech recognition, touch and stylus recognition, gesture recognition both on screen and adjacent to the screen, air gestures, head and eye tracking, voice and speech, vision, touch, gestures, and machine intelligence. Other examples of a NUI include motion gesture detection using accelerometers/gyroscopes, facial recognition, 3D displays, head, eye, and gaze tracking, immersive augmented reality and virtual reality systems, all of which provide a more natural interface, as well as technologies for sensing brain activity using electric field sensing electrodes (EEG and related methods). Thus, in one specific example, the operating system 812 or applications 814 can comprise speech-recognition software as part of a voice user interface that allows a user to operate the device 800 via voice commands. Further, the device 800 can comprise input devices and software that allows for user interaction via a user's spatial gestures, such as detecting and interpreting gestures to provide input for controlling the device and reconfiguring the user interface as described above.

A wireless modem 860 can be coupled to an antenna (not shown) and can support two-way communications between the processor 810 and external devices, as is well understood in the art. The modem 860 is shown generically and can include a cellular modem for communicating with the mobile communication network 804 and/or other radio-based modems (e.g., Bluetooth 864 or Wi-Fi 862). The wireless modem 860 is typically configured for communication with one or more cellular networks, such as a GSM network for data and voice communications within a single cellular network, between cellular networks, or between the mobile device and a public switched telephone network (PSTN).

The mobile device can further include at least one input/output port 880, a power supply 882, a satellite navigation system receiver 884, such as a Global Positioning System (GPS) receiver, an accelerometer 886, and/or a physical connector 890, which can be a USB port, IEEE 1394 (FireWire) port, and/or RS-232 port. The illustrated components 802 are not required or all-inclusive, as any components can be deleted and other components can be added.

In view of the many possible embodiments to which the principles of the disclosed invention may be applied, it should be recognized that the illustrated embodiments are only preferred examples and should not be taken as limiting in scope. Rather, the scope of protection is defined by the following claims.

The invention claimed is:

1. A liquid sampling device for use with a mobile device, comprising:
    a wired connection for connecting the liquid sampling device to the mobile device;
    a sample receiving and testing section capable of receiving a liquid sample and conducting electrochemical testing of the liquid sample; and
    a sample testing circuit configured to communicate at least one liquid sample test result to the mobile device via the wired connection, wherein the sample testing circuit comprises a modulation/demodulation circuit configured to modulate the at least one liquid sample test result into an audio signal and communicate the audio signal to the mobile device via an audio jack of the mobile device.

2. The liquid sampling device of claim 1, wherein the sample receiving and testing section comprises a sensor configured to test for nitrate concentration in the liquid sample.

3. The liquid sampling device of claim 2, wherein the sensor comprises a reference electrode, a working electrode and a counter electrode.

4. The liquid sampling device of claim 1, wherein the wired connection comprises a wired connection to an audio jack of the mobile device.

5. A data storage device encoded with a computer program, the program comprising instructions that when executed by one or more computers cause the one or more computers to perform operations comprising:
    receiving data from an attached liquid sampling device via a wired connection, the data comprising at least one liquid sample test result;
    communicating the data and position information corresponding to the data over a network; and
    displaying the at least one test result on a map to indicate a location correlated with the test result.

6. The device of claim 5, wherein the data storage device is a mobile device, wherein the one or more computers comprises the mobile device, and wherein receiving data comprises receiving data via a wired connection to an audio jack of the mobile device.

7. The device of claim 5, wherein the at least one liquid sample test result comprises an indication of a nitrate concentration.

8. The device of claim 5, wherein communicating the data and position information comprises posting the data and position information to a social network.

9. The device of claim 5, further comprising displaying a signal wave settings screen and requesting a user to select at least one of a signal wave category, an amplitude range, a frequency range and a sampling rate.

10. The device of claim 5, further comprising displaying a bias voltage settings screen and requesting a user to select at least one of a bias voltage, an amplitude, a frequency, a sampling rate, and a number of samples.

11. The device of claim 5, further comprising displaying an analysis screen and requesting a user to input a down sampling rate.

12. The device of claim 5, further comprising displaying a parameters screen and requesting a user to specify a number of stabilizing cycles.

13. The device of claim 5, further comprising displaying a parameters screen and requesting a user to specify an analysis duration.

14. The device of claim 5, wherein receiving the data comprises receiving user data entered by a user of the liquid sampling device and wherein communicating the data and position information further comprises communicating the user data.

15. The device of claim 14, wherein the user data comprises field observations entered by a user.

16. The device of claim 5, further comprising controlling a sensor in the liquid sampling device by commands entered on the mobile device and communicated via the wired connection.

17. A method of developing liquid sampling data using a liquid sampling device linked to a mobile device, comprising:
    receiving data from the liquid sampling device via the linked mobile device, the data comprising at least one liquid sampling result;
    displaying the at least one liquid sampling result on a map to indicate a location correlated with the test result; and
    updating a data structure to include the received data together with related data.

18. The method of claim 17, wherein receiving data from the liquid sampling device comprises receiving data via a wired connection to an audio jack of the mobile device.

19. The method of claim 17, wherein the at least one liquid sampling result comprises an indication of a nitrate concentration.

20. The method of claim 17, further comprising controlling a sensor in the liquid sampling device by commands entered on the mobile device and communicated via the wired connection.

* * * * *